United States Patent
Kashi (10) Patent No.: US 10,039,457 B2
(45) Date of Patent: Aug. 7, 2018

(54) ELECTRONIC CIRCUIT WITH LIGHT SENSOR, VARIABLE RESISTANCE AND AMPLIFIER

(71) Applicant: Intel Corporation, Santa Clara, CA (US)

(72) Inventor: Mostafa Kashi, Santa Clara, CA (US)

(73) Assignee: INTEL CORPORATION, Santa Clara, CA (US)

( * ) Notice: Subject to any disclaimer, the term of this patent is extended or adjusted under 35 U.S.C. 154(b) by 279 days.

(21) Appl. No.: 14/751,768

(22) Filed: Jun. 26, 2015

(65) Prior Publication Data
US 2016/0374573 A1    Dec. 29, 2016

(51) Int. Cl.
    *A61B 5/02*    (2006.01)
    *A61B 5/024*   (2006.01)
    *H03F 3/45*    (2006.01)
    *H03F 3/08*    (2006.01)

(52) U.S. Cl.
    CPC ......... *A61B 5/02427* (2013.01); *H03F 3/087* (2013.01); *H03F 3/45475* (2013.01); *A61B 2562/0233* (2013.01); *H03F 2200/261* (2013.01)

(58) Field of Classification Search
    CPC .................. A61B 5/02416; A61B 5/0261
    See application file for complete search history.

(56) References Cited

U.S. PATENT DOCUMENTS

| | | |
|---|---|---|
| 4,889,985 A | 12/1989 | Allsop et al. |
| 2006/0028156 A1 | 2/2006 | Jungwirth |
| 2007/0164752 A1 | 7/2007 | Kato |
| 2010/0268056 A1 | 10/2010 | Picard et al. |
| 2012/0215431 A1* | 8/2012 | Miyazawa ............ F02P 3/0552 701/115 |

FOREIGN PATENT DOCUMENTS

KR    101125236 B1    3/2012

OTHER PUBLICATIONS

National Semiconductor LMH6703 1.2 GHz, Low Distortion Op Amp with Shutdown, May 2005, 1-13.*
International Search Report and Written Opinion dated Aug. 30, 2016 for International Application No. PCT/US2016/033803, 14 pages.

* cited by examiner

*Primary Examiner* — Hien Nguyen
(74) *Attorney, Agent, or Firm* — Schwabe, Williamson & Wyatt, P.C.

(57) ABSTRACT

Embodiments include circuits, apparatuses, and systems for optical heart rate monitor light sensor amplifiers. In embodiments, an electronic circuit may include a differential amplifier having an inverting terminal, a non-inverting terminal, and an output terminal; a first variable resistance circuit coupled with a reference voltage, the inverting terminal of the differential amplifier, and the output terminal of the differential amplifier; a second variable resistance circuit coupled with the non-inverting terminal of the differential amplifier and the reference voltage; and a light sensor to generate an electrical signal in response to light reflected by skin of a user, the light sensor coupled with the non-inverting terminal and the inverting terminal of the differential amplifier. Other embodiments may be described and claimed.

20 Claims, 3 Drawing Sheets

FIG. 3

ELECTRONIC CIRCUIT WITH LIGHT SENSOR, VARIABLE RESISTANCE AND AMPLIFIER

FIELD

Embodiments of the present invention relate generally to the technical field of electronic circuits, and more particularly to optical heart rate monitor light sensor amplifiers.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure. Unless otherwise indicated herein, the approaches described in this section are not prior art to the claims in the present disclosure and are not admitted to be prior art by inclusion in this section.

Existing optical heart rate monitor (OHRM) light sensor amplifier circuits may use a large number of parts, such as multiple operational amplifiers (op-amps) and/or multiplexers resulting in a large footprint and cost. Existing OHRM light sensor amplifier circuits may also have performance issues relating to power consumption and excessive noise or slow response times at high gains.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example and not by way of limitation in the figures of the accompanying drawings.

DETAILED DESCRIPTION

In the following detailed description, reference is made to the accompanying drawings that form a part hereof wherein like numerals designate like parts throughout, and in which is shown by way of illustration embodiments that may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrases "A and/or B" and "A or B" mean (A), (B), or (A and B). For the purposes of the present disclosure, the phrase "A, B, and/or C" means (A), (B), (C), (A and B), (A and C), (B and C), or (A, B, and C).

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

As used herein, the term "circuitry" may refer to, be part of, or include an Application Specific Integrated Circuit (ASIC), an electronic circuit, a processor (shared, dedicated, or group), a combinational logic circuit, and/or other suitable hardware components that provide the described functionality. As used herein, "computer-implemented method" may refer to any method executed by one or more processors, a computer system having one or more processors, a mobile device such as a smartphone (which may include one or more processors), a tablet, a laptop computer, a set-top box, a gaming console, and so forth.

Figure 1:
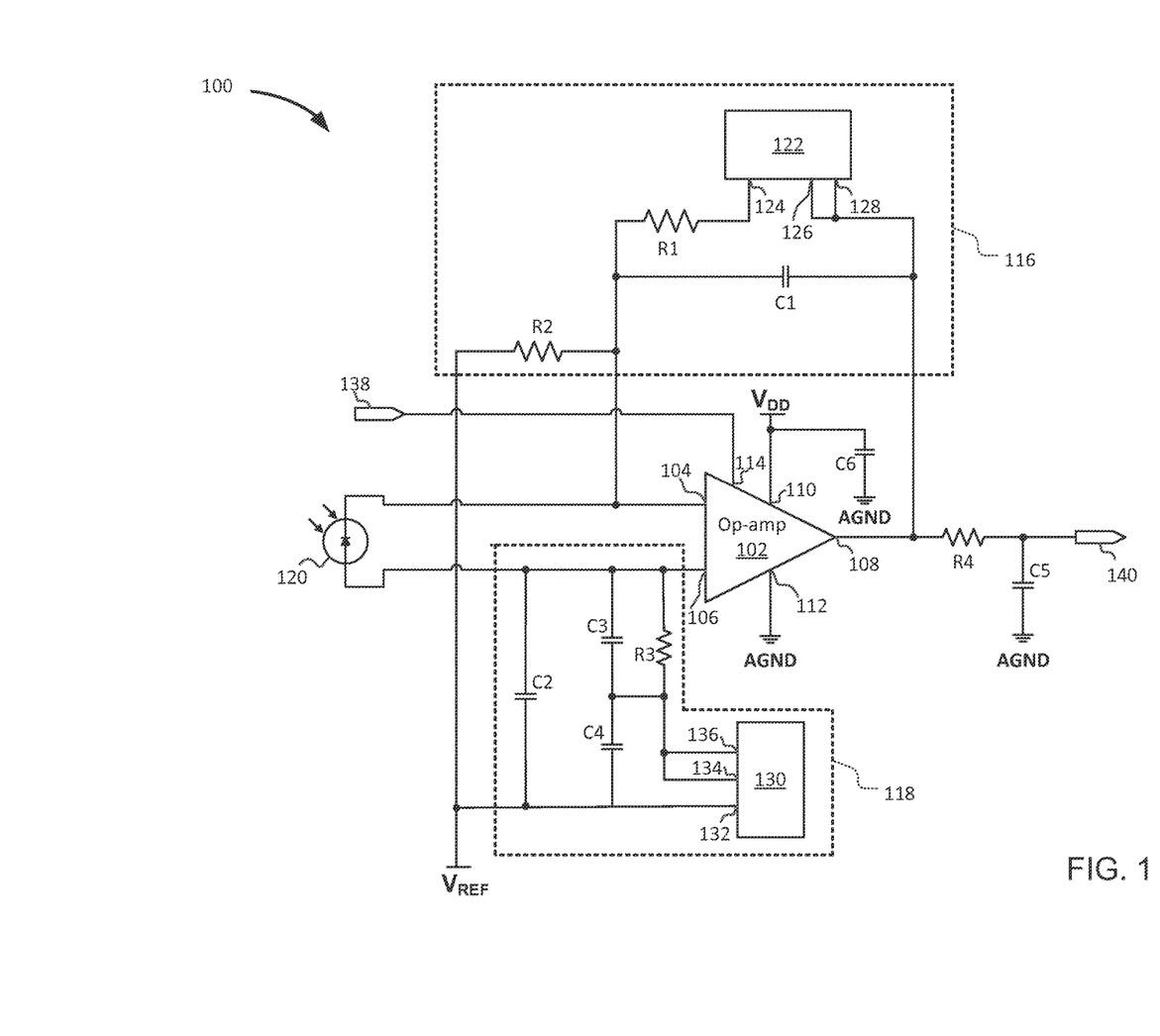
FIG. 1 illustrates an electronic circuit suitable for use in an optical heart rate monitor, in accordance with various embodiments.

FIG. 1 schematically illustrates an electronic circuit suitable for use in an optical heart rate monitor (hereinafter "circuit 100") in accordance with various embodiments. In embodiments, the circuit 100 may be an optical heart rate monitor light sensor amplifier circuit. As shown, the circuit 100 may include a differential amplifier such as an operational amplifier (op-amp) 102 having an inverting terminal 104, a non-inverting terminal 106, and an output terminal 108. In various embodiments, the op-amp 102 may also include a positive supply terminal 110, a negative supply terminal 112, and a shutdown terminal 114. In embodiments, the positive supply terminal 110 may be coupled with a positive voltage supply, $V_{DD}$, and the negative supply terminal 112 may be coupled with ground, AGND. In some embodiments, the op-amp 102 may be a low-noise, low-distortion, wide-band, rail-to-rail op-amp such as model MAX4488 manufactured by Maxim Integrated Products, Inc.

A first variable resistance circuit 116 may be electrically coupled with a reference voltage, $V_{REF}$, the inverting terminal 104, and the output terminal 108 in various embodiments. A second variable resistance circuit 118 may be electrically coupled with the reference voltage $V_{REF}$ and the non-inverting terminal 106 in some embodiments. In various embodiments, $V_{REF}$ may be ground, AGND. In some embodiments, $V_{REF}$ may be a voltage other than ground to provide a voltage offset. In embodiments, the $V_{REF}$ may be provided by a digital to analog converter (DAC) output.

A light sensor 120 may be electrically coupled with the inverting terminal 104 and the non-inverting terminal 106 in various embodiments. The light sensor 120 may generate an electrical signal in response to light reflected by skin of a user in various embodiments. In some embodiments, the light sensor 120 may be a photodiode such as model SFH2430 manufactured by Osram Opto Semiconductors GmbH, for example. In some embodiments, a first terminal of the light sensor 120 may be coupled with the non-inverting terminal 106 and a second terminal of the light sensor may be coupled with ground. In various embodiments, the second terminal of the light sensor may be coupled with the inverting terminal 104 which may provide increased speed in the circuit 100 by reducing the effects of internal capacitance in the light sensor 120.

The first variable resistance circuit 116 may include a first digital potentiometer 122 having an adjustable resistance $R_{DP1}$ on a path between the inverting terminal 104 and the output terminal 108. In some embodiments, the first digital potentiometer 122 may have a first terminal 124, a second terminal 126, and a third terminal 128. In various embodiments, the first terminal 124 may be a high terminal, the second terminal 126 may be a wiper terminal, and the third terminal 128 may be a low terminal. The second variable resistance circuit 118 may include a second digital potentiometer 130 having an adjustable resistance $R_{DP2}$ on a path between the non-inverting terminal and the reference voltage $V_{REF}$. The second digital potentiometer 130 may have a first terminal 132, a second terminal 134, and a third terminal 136. In various embodiments, the first terminal 132 may be a high terminal, the second terminal 134 may be a wiper terminal, and the third terminal 136 may be a low terminal.

In some embodiments, the first digital potentiometer 122 and the second digital potentiometer 130 may be included in a single integrated circuit such as a model ISL23428 dual 128-tap low voltage digitally controlled potentiometer manufactured by Intersil Corporation. Although not shown, the first digital potentiometer 122 and the second digital potentiometer 130 may include control signal input terminals that allow their adjustable resistance to be set by a controller such as a processor by receiving a control signal from the controller. In some embodiments, one control signal input terminal may be used for both the first digital potentiometer 122 and the second digital potentiometer 130 when they are on the same integrated circuit. In embodiments, the control signal input terminal may allow serial data input such as that based on a serial peripheral interface (SPI) protocol.

In some embodiments, the first variable resistance circuit 116 may include a first resistor R1, a second resistor R2, and a capacitor C1. The resistor R1 may have a first terminal coupled with the inverting terminal 104 and a second terminal coupled with the first terminal 124. The resistor R2 may have a first terminal coupled with the inverting terminal 104 and a second terminal coupled with the reference voltage, $V_{REF}$. The capacitor C1 may have a first terminal coupled with the inverting terminal 104 and a second terminal coupled with the output terminal 108. The second terminal 126 and the third terminal 128 of the first digital potentiometer 122 may be coupled with the output terminal 108 in various embodiments.

In some embodiments, the second variable resistance circuit 118 may include a third resistor R3 and capacitors C2, C3, and C4. The resistor R3 may have a first terminal coupled with the non-inverting terminal 106 of the op-amp 102 and a second terminal coupled with the third terminal 136 of the second digital potentiometer 130. The capacitor C2 may have a first terminal coupled with the non-inverting terminal 106 and a second terminal coupled with the reference voltage $V_{REF}$. The capacitor C3 may have a first terminal coupled with the non-inverting terminal 106 and a second terminal coupled with the second terminal of the resistor R3. The capacitor C4 may have a first terminal coupled with the second terminal of the resistor R3 and a second terminal coupled with the reference voltage $V_{REF}$. The second terminal 134 and the third terminal 136 of the second digital potentiometer 130 may be coupled with the second terminal of the resistor R3 in various embodiments. In embodiments, the circuit 100 may include a shutdown input terminal 138 coupled with the shutdown terminal 114 to receive a shutdown mode control signal from a controller such as a processor. In embodiments, the circuit 100 may include an output terminal 140 that may be coupled with a node connecting the resistor R4 and the capacitor C5 to provide an output signal to a controller such as a processor.

In some embodiments, the first variable resistance circuit 116 may be used to set a coarse gain of the circuit 100 and the second variable resistance circuit 118 may be used to set a fine gain of the circuit 100. In embodiments, an approximate gain may be set by the total resistance of R3 and $R_{DP2}$ for the fine gain and may be based at least in part on R1, R2, and $R_{DP1}$ for the coarse gain. In some embodiments, an approximate output voltage $V_{out}$ at the output terminal 108 of the op-amp 102 may be determined based at least in part on a current flowing through the light sensor 120, $I_{pd}$, with $V_{out} \approx (I_{pd}*(R3+R_{DP2}))*((R_{DP1}+R1)/R2)+1)$. In embodiments, the lowest non-inverting gain may be based at least in part on R1, R2, and a digital potentiometer wiper resistance: (R1+first digital potentiometer 122 wiper resistance)/R2. In various embodiments, R1 may be approximately 340 Ohms, R2 may be approximately 392 Ohms, and the wiper resistance of the first digital potentiometer 122 may be approximately 52 Ohms such that the lowest non-inverting gain contribution is ((340+52)/392)+1=2. In various embodiments, the first digital potentiometer 122 may be a 100 kiloohm (kΩ) digital potentiometer with 128 steps in a range from 0Ω to 100 kΩ. In embodiments, a series of eight steps may be used, using steps of 0, 1, 3, 7, 15, 31, 63, and 127 for approximate gains of 2, 4, 8, 16, 32, 64, 128, and 256 respectively. In some embodiments, R3 may be approximately 80.6 kΩ, C1 may be approximately 100 picoFarads (pF), C2 may be approximately 22 pF. C3 may be approximately 51 pF, C4 may be approximately 22 pF, C5 may be approximately 51 pF, and C6 may be approximately 1 microFarad.

In various embodiments, the capacitors C1, C2, C3, and C4 may help to reduce oscillation of the op-amp 102 and/or reduce overshoot or gain peaking in high gain scenarios. Generally, the capacitor C1 may help reduce oscillation and/or overshoot for higher gains and the capacitors C2, C3, and C4 may help reduce oscillation and/or overshoot for lower gains.

Figure 2:
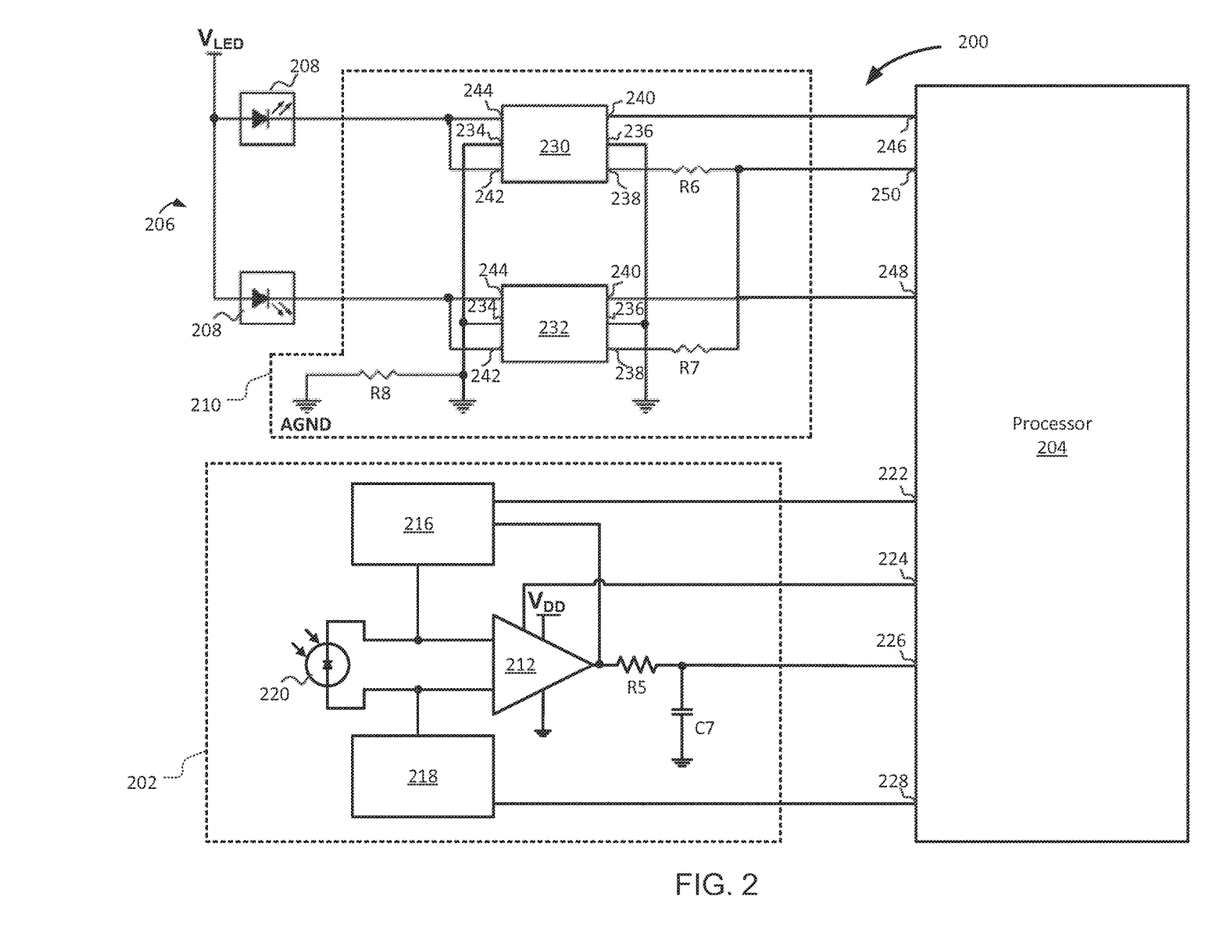
FIG. 2 illustrates an electronic device that includes the electronic circuit of FIG. 1, in accordance with various embodiments.

FIG. 2 illustrates an electronic device 200 that includes a light sensor amplifier circuit 202 (hereinafter "amplifier circuit 202"), in accordance with various embodiments. In some embodiments, the electronic device 200 may be an optical heart rate monitor system. As shown, the electronic device 200 may include a processor 204 and a light circuit 206 coupled together and configured to cooperate with each other to sense a heart rate of a user. In embodiments, the amplifier circuit 202 may be the circuit 100 described with respect to FIG. 1. The light circuit 206 may include at least one light source such as light emitting diodes (LEDs) 208. The light circuit 206 may include an LED driver circuit 210 that may be configured to allow the processor 204 to adjust an intensity of the LEDs 208 in various embodiments. The processor 204 may include one or more components, including a plurality of input and/or output terminals in various embodiments.

The amplifier circuit 202 may include an op-amp 212, a first variable resistance circuit 216, a second variable resistance circuit 218, and a light sensor 220 in various embodiments. In some embodiments, the op-amp 212 may correspond to the op-amp 102, the first variable resistance circuit 216 may be configured as described for the first variable resistance circuit 116, and the second variable resistance circuit 218 may be configured as described for the second variable resistance circuit 118. In embodiments, the processor 204 may include a first terminal 222, a second terminal 224, a third terminal 226, and a fourth terminal 228.

In embodiments, the first variable resistance circuit 216 may receive a control signal from the first terminal 222 and the second variable resistance circuit 218 may receive a control signal from the fourth terminal 228. In some embodiments, control signals from a single terminal of the processor 204 may be used to adjust the first variable resistance circuit 216 and the second variable resistance circuit 218. In some embodiments, the first variable resistance circuit 216 may include a first digital potentiometer and the second variable resistance circuit 218 may include a second digital potentiometer, both of which may be included in a single integrated circuit that allows adjustment of both digital potentiometers using control signals received at the same input terminal. In some embodiments, the control signals may be in SPI format and the IC including the digital potentiometers may include an SPI interface to allow serial data input received from the processor 204.

In some embodiments, the amplifier circuit 202 may include a resistor R5 and a capacitor C7 that may be configured at the output terminal of the op-amp 212 as described with respect to resistor R4 and capacitor C5 in FIG. 1. In various embodiments, the processor 204 may receive an output from the amplifier circuit 202 at the third terminal 226. In some embodiments, the processor 204 may provide a shutdown signal from the second terminal 224 to a shutdown terminal of the op-amp 212. In embodiments, the shutdown signal may be a digital signal and the op-amp 212 may enter a shut-down mode when a low signal such as a voltage less than or equal to $0.3*V_{DD}$ is received at the shutdown terminal and the op-amp 212 may operate in a standard mode when a high signal such as a voltage greater than or equal to $0.7*V_{DD}$ and less than or equal to $V_{DD}$ is received from the processor 204 at the shutdown terminal.

In various embodiments, the LED driver circuit 210 may include a first LED driver 230 and a second LED driver 232. The first and second LED drivers 230, 232 may be low-dropout LED drivers such as model AS1111A manufactured by ams AG in some embodiments. Each of the first and second LED drivers 230 and 232 may include a first ground terminal 234, a second ground terminal 236, a control terminal 238, an enable terminal 240, a first input terminal 242, and a second input terminal 244. The LED drivers 230, 232 may have a different number or different types of terminals in various embodiments.

The processor 204 may include a fifth terminal 246 and a sixth terminal 248 coupled with the enable terminal 240 of the first LED driver 230 and the enable terminal 240 of the second LED driver 232, respectively. The processor 204 may include a seventh terminal 250 to send a control signal to the control terminal 238 of the first LED driver 230 and the control terminal 238 of the second LED driver 232. In some embodiments, the LED driver circuit 210 may include a resistor R6 between the control terminal 238 of the first LED driver 230 and the seventh terminal 250. The LED driver circuit may also include a resistor R7 between the control terminal 238 of the second LED driver circuit 232 and the seventh terminal 250. In various embodiments, the processor 204 may include a different number and/or different types of input or output terminals and may be coupled with the LED driver circuit 210 and/or the amplifier circuit 202 in a different manner.

In various embodiments, the first ground terminals 234 of the first and second LED drivers 230 and 232 may be electrically coupled with ground. The second ground terminals 236 of the first and second LED drivers 230 and 232 may also be electrically coupled with ground. In some embodiments, a resistor R8 may be positioned between an analog ground AGND and the ground coupled with first and second ground terminals 234 and 236. In some embodiments, the first input terminal 242 and the second input terminal 244 of the first LED driver 230 may be coupled with a cathode of a first LED 208. Similarly, the first and second input terminals 242 and 244 respectively of the second LED driver 232 may be coupled with a cathode of a second LED 208. The anodes of the LEDs 208 may be electrically coupled with a voltage VIED.

In some embodiments, the electronic device 200 may take samples approximately 30 to 40 times per second. In some embodiments, the time for taking each sample may be within a range of approximately 20 to 60 microseconds. In various embodiments, the electronic device 200 may take samples at a different rate and/or may take a different period of time to take each sample. In taking a sample, the processor 204 may send signals to the LED driver circuit 210 to cause the LEDs 208 to burst on with an initial intensity of approximately 25 percent of their maximum intensity. The processor 204 may send additional signals to the amplifier circuit 202 to take the op-amp 212 out of shutdown mode and set digital potentiometers in the first variable resistance circuit 216 and the second variable resistance circuit 218 to adjust a gain of the amplifier circuit 202. The light sensor 220 may receive light from the LEDs 208 reflected from the skin of a user and generate a signal that may be amplified by the amplifier circuit 202. The processor 204 may receive an output from the amplifier circuit 202.

Based at least in part on the received output from the amplifier circuit 202, the processor 204 may send signals to the amplifier circuit 212 to alter resistance values of one or more digital potentiometers to increase a gain of the amplifier circuit 212 if the received output is below a predefined value. The processor 204 may also send signals to the LED driver circuit 210 to increase an intensity of the LEDs 208 if the amplifier circuit 202 is already set for maximum gain and the received output is still below a predefined value. In various embodiments, the processor 204 may also send one or more signals to the LED driver circuit 210 or the amplifier circuit 202 to reduce an intensity of the LEDs 208 or reduce a gain of the amplifier circuit 202. In some embodiments, the processor 204 may send signals to keep the received output within a predefined range of values between a predefined lower value and a predefined upper value.

After a sample has been collected by the processor 204, the processor 204 may send one or more signals to the LED driver circuit 210 and/or the amplifier circuit 202 to cause them to enter a shut-down mode or standby mode to reduce power consumption while a sample is not being collected. In various embodiments, adjusting an intensity of the LEDs 208 or a gain of the amplifier circuit 202 may allow the electronic device 200 to effectively determine a heart rate of users having different skin tones due to the range of skin reflectivity associated with different skin tones. In some embodiments, the processor 204 may store settings for the LED driver circuit 210 and/or the amplifier circuit 202 and associate them with an identifier for a particular user. In taking a sample, the processor 204 may send initial signals based at least in part on the stored settings and send additional signals to keep the output within the predefined range if needed.

Figure 3:
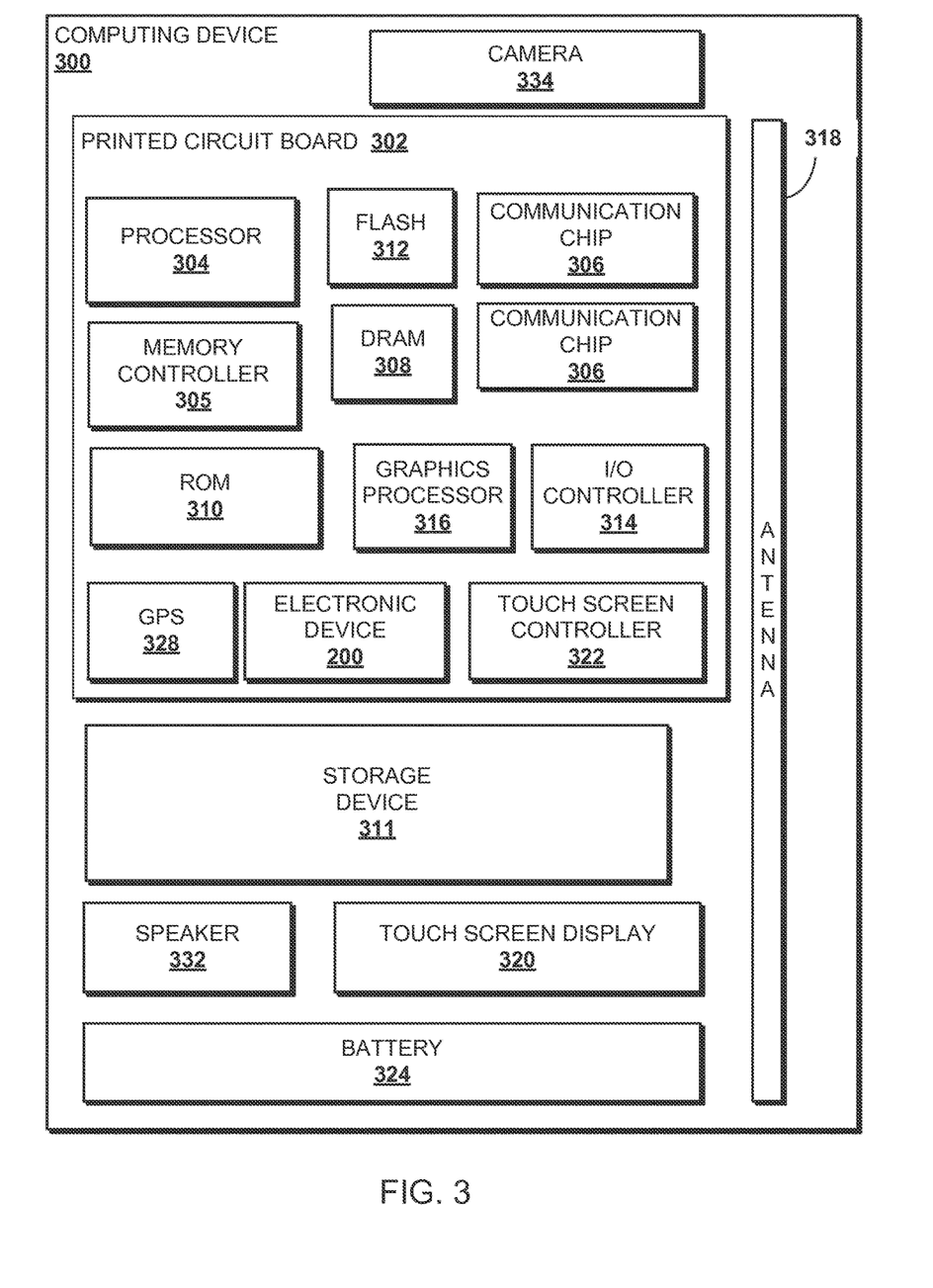
FIG. 3 illustrates an example computing device configured to employ the devices and circuits described herein, in accordance with various embodiments.

FIG. 3 illustrates an example computing device 300 that may employ the devices or circuits and/or portions thereof described herein (e.g., circuits 100 or electronic device 200), in accordance with various embodiments. As shown, computing device 300 may include a number of components, such as one or more processor(s) 304 (one shown) and at least one communication chip 306. In various embodiments, the one or more processor(s) 304 each may include one or more processor cores. In various embodiments, the at least one communication chip 306 may be physically and electrically coupled to the one or more processor(s) 304. In further implementations, the communication chip 306 may be part of the one or more processor(s) 304. In various embodiments, computing device 300 may include printed circuit board (PCB) 302. For these embodiments, the one or more processor(s) 304 and communication chip 306 may be disposed thereon. In alternate embodiments, the various components may be coupled without the employment of PCB 302.

Depending on its applications, computing device 300 may include other components that may or may not be physically and electrically coupled to the PCB 302, e.g., electronic device 200. These other components may include, but are not limited to, memory controller 305, volatile memory (e.g., dynamic random access memory (DRAM) 308), non-volatile memory such as read only memory (ROM) 310, flash memory 312, storage device 311 (e.g., a hard-disk drive (HDD)), an I/O controller 314, a digital signal processor (not shown), a crypto processor (not shown), a graphics processor 316, one or more antenna 318, a display (not shown), a touch screen display 320, a touch screen controller 322, a battery 324, an audio codec (not shown), a video codec (not shown), a global positioning system (GPS) device 328, an accelerometer (not shown), a gyroscope (not shown), a speaker 332, a camera 334, and a mass storage device (such as hard disk drive, a solid state drive, compact disk (CD), digital versatile disk (DVD)) (not shown), a power management unit (PMU) not shown), and so forth. In various embodiments, the processor 304 may be integrated on the same die with other components to form a System on Chip (SoC). In embodiments, devices, circuits, and/or portions thereof described herein (e.g., circuits 100 or electronic device 200) may be implemented in any digital and/or analog circuits of the computing device 300. In some embodiments, the processor 304 may also serve as the processor 204 of the electronic device 200.

In some embodiments, the one or more processor(s) 304, flash memory 312, and/or storage device 311 may include associated firmware (not shown) storing programming instructions configured to enable computing device 300, in response to execution of the programming instructions by one or more processor(s) 304, to practice all or selected aspects of operating system and/or application methods. In various embodiments, these aspects may additionally or alternatively be implemented using hardware separate from the one or more processor(s) 304, flash memory 312, or storage device 311.

In various embodiments, one or more components of the computing device 300 may include the circuit 100 and/or the electronic device 200 described herein instead.
For example, the circuit 100 and/or the electronic device 200 may be included in I/O controller 314, processor 304, memory controller 305, and/or another component of computing device 300. In some embodiments, the circuit 100 and/or the electronic device 200 may be included in the processor 304. In embodiments, the processor 304 or another component of the computing device 300 may include a plurality of circuits 100 and/or electronic devices 200.

The communication chips 306 may enable wired and/or wireless communications for the transfer of data to and from the computing device 300. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. The communication chip 306 may implement any of a number of wireless standards or protocols, including but not limited to IEEE 702.20, Long Term Evolution (LTE), LTE Advanced (LTE-A), General Packet Radio Service (GPRS), Evolution Data Optimized (Ev-DO), Evolved High Speed Packet Access (HSPA+), Evolved High Speed Downlink Packet Access (HSDPA+), Evolved High Speed Uplink Packet Access (HSUPA+), Global System for Mobile Communications (GSM), Enhanced Data rates for GSM Evolution (EDGE), Code Division Multiple Access (CDMA), Time Division Multiple Access (TDMA), Digital Enhanced Cordless Telecommunications (DECT), Worldwide Interoperability for Microwave Access (WiMAX), Bluetooth, derivatives thereof, as well as any other wireless protocols that are designated as 3G, 4G, 5G, and beyond. The computing device 300 may include a plurality of communication chips 306. For instance, a first communication chip 306 may be dedicated to shorter range wireless communications such as Wi-Fi, near field communication (NFC), and Bluetooth, and a second communication chip 306 may be dedicated to longer range wireless communications such as GPS, EDGE, GPRS, CDMA, WiMAX, LTE, Ev-DO, and others.

In various implementations, the computing device 300 may be a laptop, a netbook, a notebook, an ultrabook, a smartphone, a computing tablet, a personal digital assistant (PDA), an ultra-mobile PC, a mobile phone, a desktop computer, a server, a printer, a scanner, a monitor, a set-top box, an entertainment control unit (e.g., a gaming console or automotive entertainment unit), a digital camera, an appliance, a portable music player, an internet of things (IoT) device, a wearable device, or a digital video recorder. In further implementations, the computing device 300 may be any other electronic device that processes digital or analog data or signals. In some embodiments, the computing device 300 may be a system that may employ the devices or circuits and/or portions thereof described herein (e.g., circuit 100 or electronic device 200), in accordance with various embodiments.

Some non-limiting Examples are presented below.

Example 1 may include an electronic circuit comprising: a differential amplifier having an inverting terminal, a non-inverting terminal, and an output terminal; a first variable resistance circuit coupled with a reference voltage, the inverting terminal of the differential amplifier, and the output terminal of the differential amplifier; a second variable resistance circuit coupled with the non-inverting terminal of the differential amplifier and the reference voltage; and a light sensor to generate an electrical signal in response to light reflected by skin of a user, the light sensor coupled with the non-inverting terminal of the differential amplifier and the inverting terminal of the differential amplifier.

Example 2 may include the subject matter of Example 1, wherein the differential amplifier is an operational amplifier (op-amp).

Example 3 may include the subject matter of Example 2, wherein the first variable resistance circuit includes a digital potentiometer having an adjustable resistance on a path between the inverting terminal of the op-amp and the output terminal of the op-amp.

Example 4 may include the subject matter of Example 2, wherein the second variable resistance circuit includes a digital potentiometer having an adjustable resistance on a path between the non-inverting terminal of the op-amp and the reference voltage.

Example 5 may include the subject matter of Example 2, wherein: the first variable resistance circuit includes a first digital potentiometer having a first adjustable resistance on a first path between the inverting terminal of the op-amp and the output terminal of the op-amp; and the second variable resistance circuit includes a second digital potentiometer having a second adjustable resistance on a second path between the non-inverting terminal of the op-amp and the reference voltage.

Example 6 may include the subject matter of Example 5, wherein: the first variable resistance circuit includes a first resistor having a first terminal coupled with the inverting terminal of the op-amp and a second terminal coupled with the reference voltage; the first variable resistance circuit includes a second resistor having a first terminal coupled with the inverting terminal of the op-amp and a second terminal coupled with a first terminal of the first digital potentiometer, a second terminal of the first digital potentiometer is coupled with the output terminal of the op-amp; the second variable resistance circuit includes a third resistor having a first terminal coupled with the non-inverting terminal of the op-amp and a second terminal coupled with a first terminal of the second digital potentiometer; and a second terminal of the second digital potentiometer is coupled with the reference voltage.

Example 7 may include the subject matter of any one of Examples 2-6, wherein: the first variable resistance circuit includes a first capacitor having a first terminal coupled with the inverting terminal of the op-amp and a second terminal coupled with the output terminal of the op-amp; and the second variable resistance circuit includes a second capacitor having a first terminal coupled with the non-inverting terminal of the op-amp and a second terminal coupled with the reference voltage.

Example 8 may include the subject matter of any one of Examples 1-7, wherein the reference voltage is ground.

Example 9 may include the subject matter of any one of Examples 1-8, wherein the light sensor includes a photodiode.

Example 10 may include the subject matter of any one of Examples 5-8, wherein the first digital potentiometer and the second digital potentiometer are included in a single integrated circuit.

Example 11 may include an electronic circuit comprising: an operational amplifier (op-amp) having an inverting terminal, a non-inverting terminal, and an output terminal; a first variable resistance circuit coupled with a reference voltage, the inverting terminal of the op-amp, and the output terminal of the op-amp; a second variable resistance circuit coupled with the non-inverting terminal of the op-amp and the reference voltage; and a light sensor to generate an electrical signal in response to light reflected by skin of a user, the light sensor coupled with the non-inverting terminal of the op-amp and the inverting terminal of the op-amp, wherein the op-amp is the only op-amp in the electronic circuit.

Example 12 may include the subject matter of Example 11, wherein the op-amp includes a shutdown terminal and the op-amp is to enter a shut-down mode in response to a shutdown signal received at the shutdown terminal.

Example 13 may include the subject matter of any one of Examples 11-12 wherein: the first variable resistance circuit includes a first digital potentiometer having a first adjustable resistance on a first path between the inverting terminal of the op-amp and the output terminal of the op-amp; and the second variable resistance circuit includes a second digital potentiometer having a second adjustable resistance on a second path between the non-inverting terminal of the op-amp and a reference voltage.

Example 14 may include the subject matter of Example 13, wherein: the first adjustable resistance is set in response to a first control signal; and the second adjustable resistance is set in response to a second control signal.

Example 15 may include the subject matter of any one of Examples 11-14, wherein the light sensor includes a photodiode.

Example 16 may include an optical heart rate monitor system comprising: a processor; a light source; a light sensor to generate an electrical signal in response to light from the light source reflected by skin of a user; and an amplifier circuit coupled with the light sensor and the processor, wherein the amplifier circuit includes: an operational amplifier (op-amp) having an inverting terminal, a non-inverting terminal, and an output terminal; a first variable resistance circuit coupled with a reference voltage, the inverting terminal of the op-amp, and the output terminal of the op-amp; and a second variable resistance circuit coupled with the non-inverting terminal of the op-amp and the reference voltage, wherein the light sensor is coupled with the non-inverting terminal of the op-amp and the inverting terminal of the op-amp.

Example 17 may include the subject matter of Example 16, wherein: the first variable resistance circuit includes a first digital potentiometer coupled with the processor; the second variable resistance circuit includes a second digital potentiometer coupled with the processor, the first digital potentiometer is to have a first resistance in response to a first control signal from the processor; and the second digital potentiometer is to have a second resistance in response to a second control signal from the processor.

Example 18 may include the subject matter of any one of Examples 16-17, wherein the light sensor is a photodiode.

Example 19 may include the subject matter of any one of Examples 16-18, wherein the op-amp includes a shutdown terminal and the op-amp is to enter a shut-down mode in response to a shutdown signal received at the shutdown terminal from the processor.

Example 20 may include the subject matter of any one of Examples 17-18, wherein the first variable resistance circuit includes a first resistor having a first terminal coupled with the inverting terminal of the op-amp and a second terminal coupled with the reference voltage; the first variable resistance circuit includes a second resistor having a first terminal coupled with the inverting terminal of the op-amp and a second terminal coupled with a first terminal of the first digital potentiometer, a second terminal of the first digital potentiometer is coupled with the output terminal of the op-amp; the second variable resistance circuit includes a third resistor having a first terminal coupled with the non-inverting terminal of the op-amp and a second terminal coupled with a first terminal of the second digital potentiometer; a second terminal of the second digital potentiometer is coupled with the reference voltage; and the reference voltage is ground.

Example 21 may include an optical heart rate monitor device comprising: means for generating an electrical signal in response to light reflected from skin of a user; means for differentially amplifying the electrical signal with a single operational amplifier (op-amp) to generate an amplified signal; and means for adjusting a gain of the means for amplifying the electrical signal based at least in part on a first variable resistance device and a second variable resistance device.

Example 22 may include the subject matter of Example 21, further comprising means for reducing oscillation of the means for differentially amplifying the electrical signal.

Example 23 may include the subject matter of any one of Examples 21-22, further comprising means for entering a shut-down mode of the means for differentially amplifying the electrical signal.

Example 24 may include the subject matter of any one of Examples 21-23, further comprising means for generating light to be reflected from skin of a user.

Example 25 may include the subject matter of Example 24, further comprising means for adjusting an intensity of the generated light.

Although certain embodiments have been illustrated and described herein for purposes of description, this application is intended to cover any adaptations or variations of the embodiments discussed herein. Therefore, it is manifestly intended that embodiments described herein be limited only by the claims.

Where the disclosure recites "a" or "a first" element or the equivalent thereof, such disclosure includes one or more such elements, neither requiring nor excluding two or more such elements. Further, ordinal indicators (e.g., first, second, or third) for identified elements are used to distinguish between the elements, and do not indicate or imply a required or limited number of such elements, nor do they indicate a particular position or order of such elements unless otherwise specifically stated.

What is claimed is:

1. An electronic circuit comprising:
   a differential amplifier having an inverting terminal, a non-inverting terminal, and an output terminal;
   a first variable resistance circuit coupled with a reference voltage, the inverting terminal of the differential amplifier, and the output terminal of the differential amplifier, wherein the first variable resistance circuit includes:
   a first potentiometer having a first adjustable resistance on a first path between the inverting terminal and the output terminal;
   a first resistor having a first terminal coupled with the inverting terminal and a second terminal coupled with the reference voltage; and
   a capacitor having a first terminal coupled with the inverting terminal and a second terminal coupled with the output terminal;
   a second variable resistance circuit coupled with the non-inverting terminal of the differential amplifier and the reference voltage, wherein the second variable resistance circuit includes a second potentiometer, different from the first potentiometer, having a second adjustable resistance on a second path between the non-inverting terminal and the reference voltage; and
   a light sensor to generate an electrical signal in response to light reflected by skin of a user, the light sensor coupled with the non-inverting terminal of the differential amplifier and the inverting terminal of the differential amplifier.

2. The electronic circuit of claim 1, wherein the differential amplifier is an operational amplifier (op-amp).

3. The electronic circuit of claim 2, wherein the first potentiometer is a digital potentiometer.

4. The electronic circuit of claim 2, wherein the second potentiometer is a digital potentiometer.

5. The electronic circuit of claim 2, wherein:
   the first potentiometer is a first digital potentiometer; and
   the second potentiometer is a second digital potentiometer.

6. The electronic circuit of claim 5, wherein:
   the first variable resistance circuit includes a second resistor having a first terminal coupled with the inverting terminal of the op-amp and a second terminal coupled with a first terminal of the first digital potentiometer;
   a second terminal of the first digital potentiometer is coupled with the output terminal of the op-amp;
   the second variable resistance circuit includes a third resistor having a first terminal coupled with the non-inverting terminal of the op-amp and a second terminal coupled with a first terminal of the second digital potentiometer; and
   a second terminal of the second digital potentiometer is coupled with the reference voltage.

7. The electronic circuit of claim 6, wherein the capacitor a first capacitor and
   the second variable resistance circuit includes a second capacitor having a first terminal coupled with the non-inverting terminal of the op-amp and a second terminal coupled with the reference voltage.

8. The electronic circuit of claim 7, wherein the reference voltage is ground.

9. The electronic circuit of claim 8, wherein the light sensor includes a photodiode.

10. The electronic circuit of claim 5, wherein the first digital potentiometer and the second digital potentiometer are included in a single integrated circuit.

11. An electronic circuit comprising:
    an operational amplifier (op-amp) having an inverting terminal, a non-inverting terminal, and an output terminal;
    a first variable resistance circuit coupled with a reference voltage, the inverting terminal of the op-amp, and the output terminal of the op-amp, wherein the first variable resistance circuit includes a first potentiometer having a first adjustable resistance on a first path between the inverting terminal and the output terminal, and the first variable resistance circuit includes a first resistor having a first terminal coupled with the inverting terminal and a second terminal coupled with the reference voltage, and also includes a second resistor having a first terminal coupled with the inverting terminal and a second terminal coupled with a first terminal of the first potentiometer;
    a second variable resistance circuit coupled with the non-inverting terminal of the op-amp and the reference voltage, wherein the second variable resistance circuit includes a second potentiometer, different from the first potentiometer, having a second adjustable resistance on a second path between the non-inverting terminal and the reference voltage; and
    a light sensor to generate an electrical signal in response to light reflected by skin of a user, the light sensor coupled with the non-inverting terminal of the op-amp and the inverting terminal of the op-amp, wherein the op-amp is the only op-amp in the electronic circuit.

12. The electronic circuit of claim 11, wherein the op-amp includes a shutdown terminal and the op-amp is to enter a shut-down mode in response to a shutdown signal received at the shutdown terminal.

13. The electronic circuit of claim 11 wherein:
the first potentiometer is a first digital potentiometer; and
the second potentiometer is a second digital potentiometer.

14. The electronic circuit of claim 13, wherein:
the first adjustable resistance is set in response to a first control signal; and
the second adjustable resistance is set in response to a second control signal.

15. The electronic circuit of claim 14, wherein the light sensor includes a photodiode.

16. An optical heart rate monitor system comprising:
a processor;
a light source;
a light sensor to generate an electrical signal in response to light from the light source reflected by skin of a user; and
an amplifier circuit coupled with the light sensor and the processor,
wherein the amplifier circuit includes:
an operational amplifier (op-amp) having an inverting terminal, a non-inverting terminal, and an output terminal;
a first variable resistance circuit coupled with a reference voltage, the inverting terminal of the op-amp, and the output terminal of the op-amp, wherein the first variable resistance circuit includes:
a first potentiometer having a first adjustable resistance on a first path between the inverting terminal and the output terminal;
a first resistor having a first terminal coupled with the inverting terminal of the op-amp and a second terminal coupled with the reference voltage; and
a capacitor having a first terminal coupled with the inverting terminal and a second terminal couple with the output terminal; and
a second variable resistance circuit coupled with the non-inverting terminal of the op-amp and the reference voltage, wherein the second variable resistance circuit includes a second potentiometer, different from the first potentiometer, having a second adjustable resistance on a second path between the non-inverting terminal and the reference voltage, and wherein the light sensor is coupled with the non-inverting terminal of the op-amp and the inverting terminal of the op-amp.

17. The optical heart rate monitor system of claim 16, wherein:
the first potentiometer is a first digital potentiometer coupled with the processor;
the second potentiometer is a second digital potentiometer coupled with the processor;
the first digital potentiometer is to have a first resistance in response to a first control signal from the processor; and
the second digital potentiometer is to have a second resistance in response to a second control signal from the processor.

18. The optical heart rate monitor system of claim 17, wherein the light sensor is a photodiode.

19. The optical heart rate monitor system of claim 17, wherein the op-amp includes a shutdown terminal and the op-amp is to enter a shut-down mode in response to a shutdown signal received at the shutdown terminal from the processor.

20. The optical heart rate monitor system of claim 17, wherein
the first variable resistance circuit includes a second resistor having a first terminal coupled with the inverting terminal of the op-amp and a second terminal coupled with a first terminal of the first digital potentiometer;
a second terminal of the first digital potentiometer is coupled with the output terminal of the op-amp;
the second variable resistance circuit includes a third resistor having a first terminal coupled with the non-inverting terminal of the op-amp and a second terminal coupled with a first terminal of the second digital potentiometer;
a second terminal of the second digital potentiometer is coupled with the reference voltage; and
the reference voltage is ground.

* * * * *

UNITED STATES PATENT AND TRADEMARK OFFICE
CERTIFICATE OF CORRECTION

PATENT NO. : 10,039,457 B2  
APPLICATION NO. : 14/751768  
DATED : August 7, 2018  
INVENTOR(S) : Kashi Page 1 of 1

It is certified that error appears in the above-identified patent and that said Letters Patent is hereby corrected as shown below:

In the Claims

Column 12  
Line 26-27, "... capacitor a first capacitor" should read -- ... capacitor is a first capacitor --

Column 13  
Line 39, "... couple" should read -- ... coupled --

Signed and Sealed this  
Seventeenth Day of September, 2019

Andrei Iancu  
*Director of the United States Patent and Trademark Office*